(12) United States Patent
Mehta

(10) Patent No.: US 12,220,341 B2
(45) Date of Patent: Feb. 11, 2025

(54) PRESSURE APPARATUS TO REDUCE SWELLING AFTER MEDICAL DEVICE IMPLANTATION AND RELATED METHOD

(71) Applicant: William Beaumont Hospital, Royal Oak, MI (US)

(72) Inventor: Nishaki Mehta, Birmingham, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 0 days.

(21) Appl. No.: 17/108,541

(22) Filed: Dec. 1, 2020

(65) Prior Publication Data
US 2021/0161698 A1   Jun. 3, 2021

Related U.S. Application Data

(60) Provisional application No. 62/943,141, filed on Dec. 3, 2019.

(51) Int. Cl.
*A61F 13/00* (2024.01)
*A61F 5/34* (2006.01)
*A61F 13/02* (2006.01)

(52) U.S. Cl.
CPC .......... *A61F 5/34* (2013.01); *A61F 13/00051* (2013.01); *A61F 13/02* (2013.01);
(Continued)

(58) Field of Classification Search
CPC ........ A61F 5/34; A61F 5/32; A61F 13/00051; A61F 13/0028; A61F 13/0054; A61F 13/02; A61F 13/0233
See application file for complete search history.

(56) References Cited

U.S. PATENT DOCUMENTS

| | | | | |
|---|---|---|---|---|
| 4,224,945 A | * | 9/1980 | Cohen | A61F 13/00063 602/53 |
| 5,514,155 A | * | 5/1996 | Daneshvar | A61B 17/1325 602/53 |

(Continued)

FOREIGN PATENT DOCUMENTS

| | | | |
|---|---|---|---|
| CN | 210843294 U | * | 6/2020 |
| EP | 2708215 A1 | | 3/2014 |

OTHER PUBLICATIONS

Translation of CN-210843294-U from PE2E Search. (Year: 2020).*

(Continued)

*Primary Examiner* — Kim M Lewis

(74) *Attorney, Agent, or Firm* — Honigman LLP; Douglas H. Siegel; Jonathan P. O'Brien

(57) ABSTRACT

A pressure system and method for managing post-operative swelling. The pressure system has a balloon with a quadrilateral basal skirt that surrounds a surgical site on a patient. A plurality of strap-receiving slots is located in the skirt. Adhesive pads are affixed to the patient outside the skirt. One or more tensioning straps are deployed between the strap-receiving slots and the adhesive pads so that tension can be applied to the straps and to the skirt in order to press the balloon upon the surgical site. Optionally, the pressure system provides visual feedback cues to enable the operator to determine appropriate compression and assess skin recoil feedback. Such visual feedback cues may signify swelling reduction and skin turgor.

9 Claims, 10 Drawing Sheets

(52) U.S. Cl.
CPC ............... *A61F 2013/0028* (2013.01); *A61F 2013/0054* (2013.01)

(56) References Cited

U.S. PATENT DOCUMENTS

| | | | | |
|---|---|---|---|---|
| 5,643,315 | A | * | 7/1997 | Daneshvar ........ A61F 13/01034 606/202 |
| 5,779,657 | A | * | 7/1998 | Daneshvar ........... A61B 17/135 602/60 |
| 5,891,070 | A | | 4/1999 | Shirouzu et al. |
| 7,927,295 | B2 | * | 4/2011 | Bates ..................... A61B 17/12 602/53 |
| 8,759,603 | B2 | | 6/2014 | Wada et al. |
| 9,789,006 | B2 | | 10/2017 | Joyner |
| 9,993,382 | B1 | | 6/2018 | Blurton et al. |
| 10,722,244 | B2 | | 7/2020 | Lakkireddy et al. |
| 2013/0085524 | A1 | | 4/2013 | Dahlberg et al. |
| 2013/0331755 | A1 | * | 12/2013 | Rotblatt ..................... A61F 5/34 602/19 |
| 2015/0209218 | A1 | | 7/2015 | Rego |
| 2015/0305958 | A1 | * | 10/2015 | Hoff .................... A61B 17/1325 601/134 |
| 2017/0156735 | A1 | * | 6/2017 | Parker ........................ A61F 5/32 |
| 2018/0000494 | A1 | | 1/2018 | Wada |
| 2021/0023181 | A1 | * | 1/2021 | Topouzi ..................... A61K 8/64 |
| 2022/0104988 | A1 | | 4/2022 | Blurton et al. |

OTHER PUBLICATIONS

Website: http://www.pressure-products.com/wip/pocket-pal.html, Pocket Pal II Device Pocket Compression Harness with Cooling Gel Pack, Copyright 2022, 2 pgs. Retrieved from Internet on Oct. 4, 2022.
Website: www.merit.com/cardiac-intervention/ep-and-crm/cardiac-rhythm-management/safeguard-focus/, "SafeGuard Focus™ & Focus Cool™ Compression Device", Merit Medical Systems, 10 pgs, Copyright 2022. Retrieved from Internet on Oct. 4, 2022.
Kalfon E. AD, et al. Clinically Significant Pocket Hematoma Increases Long-Term Risk of Device Infection: Bruise Control Infection Study. J Am Coll Cardiol. Mar. 22, 2016; 67 (11); 1300-1308.
Nagarajan, D.V., et al. Use of a pocket compression device for the prevention and treatment of pocket hematoma after pacemarker and defibrillator implantation (Stop-Hematoma-I). J. Interv Card Electrophysiol. Aug. 2017.; 49(2): 197-204.
TT MediTrade Instruction manual for Kikuhime subbandage & body pressure measuring device (2 pages).
Jul. 20, 2018 Pressure Products; http://www.pressure-products.com/wip/pocket-pal.html (11 pages).

* cited by examiner

THE FOLLOWING TABLE AND FIGURES SUMMARIZE
THE TYPICAL PROPERTIES OF SIPI-133 FILM.

| TYPICAL PROPERTIES | METHOD (ASTM) | ENGLISH/ COMMON UNITS | VALUES |
|---|---|---|---|
| PHYSICAL CHARACTERISTICS | | | |
| SPECIFIC GRAVITY | D792 | °F | 1.12 |
| MECHANICAL CHARACTERISTICS | | | |
| HARDNESS, DUROMETER, SHORE A (+/-4) | D2240 | - | 90 |
| ELONGATION AT BREAK | D412 | % | 530 |
| TENSILE STRENGTH BREAK | D412 | PSI | 4,790 |
| 100% ELONGATION | D412 | PSI | 1,400 |
| 300% ELONGATION | D412 | PSI | 3,100 |
| TEAR STRENGTH | D624 DIE C | LB/IN | 630 |
| TABER ABRASION | D-1044 | MG LOSS | 30 |
| THERMAL | | | |
| VICAT SOFTENING TEMPERATURE | D 1525 | °F(°C) | 212°F (100°C) |

FIG. 10

PRESSURE APPARATUS TO REDUCE SWELLING AFTER MEDICAL DEVICE IMPLANTATION AND RELATED METHOD

CROSS-REFERENCE TO RELATED APPLICATION

This application is a non-provisional patent application that claims the benefit of priority of U.S. provisional application Ser. No. 62/943,141, filed Dec. 3, 2019, the contents of which are hereby incorporated in their entirety by reference herein.

TECHNICAL FIELD

An aspect of the present disclosure provides, but is not limited to, an inexpensive, reliable, and easy to provide and use a compression apparatus (and a related system and method) in the medical field for preventing swelling, hematomas, and scarring or proliferative scarring with concomitant suspension capabilities (e.g., a suspension system or suspension mechanism) after device implantation.

Other aspects of the present disclosure include an apparatus, system, and method that optionally provide visual read outs of pressure exerted on the anatomical site with a feedback sensor, if used.

BACKGROUND

As more people are living longer with significant cardiac disease, permanent pacemakers (PPMs), implantable cardioverter-defibrillators (ICDs), and cardiac resynchronization therapy (CRT) devices are being implanted more frequently. Beginning early in the 21st century, there has also been an expansion in the use of cardiac implantable electronic devices (CIEDs). This term may include a permanent pacemaker device (PPM) device, an implantable cardioverter-defibrillator (ICD) device, and a cardiac resynchronization therapy (CRT) device, as well as other devices such as insertable cardiac monitors [also sometimes referred to as implantable cardiac monitors or implantable loop recorders] and left ventricular assist devices. Device therapy has become more commonplace.

Against this background, there are about 1.6 million cardiac implantable devices (pacemakers and defibrillators) implanted every year. In addition, the battery life is 6-8 years, which means most patients have 2-3 reoperations for battery changes in their lifetime. There is up to a 9% risk of bleeding following this procedure. Up to 35% of the patients undergoing this procedure are on blood thinners to prevent heart attacks, strokes and stent blockages. Management of a blood thinner around the time of surgery has been customized on an individual basis. Discontinuing the blood thinner places patients at risk for a heart attack, stroke or compromise of their stents. However, continuing the blood thinner medication puts the patient at a higher risk of bleeding (hematoma) during surgery. In up to 15% of this population, medications are held perioperatively but this increases the risk of perioperative thrombotic events like stroke. Such hematomas serve to be a nidus for bacterial infection. This is a dreaded complication since the cardiac device infection can by extension lead to heart infection due in part to a contiguous relationship therebetween. If the hematoma does not resolve, it requires reoperation and in cases of infection, possible CIED system extraction, which can be a fatal surgery.

Current practice includes tailored interruption of anticoagulation and application of a pressure dressing which is a crude method of placing a gauze stretch bandage over the surgical site. Other potential modalities include sandbag or icepacks. The efficacy of the procedure depends on the skill of the provider, unreliable application of pressure over the desired site and dislodgment of the dressing over time. In addition, patients may wear a shoulder sling to avoid dislodgement of leads overnight. A small pilot trial demonstrated that the conventional pressure dressing resulted in 3-7 mm Hg pressure. The venous pressure in most patients is over 20 mm Hg and mean arterial pressure is at least 60 mm Hg. Therefore, the current range of pressure delivered using such conventional approaches is inadequate to combat venous or arterial pressure.

In the field of vascular and interventional cardiology, there are several hemostatic devices used to compress the radial and femoral arteries. However, these arteries extend over the continuous bony surfaces such as the radius and femur bones, respectively. In contrast, CIEDs are generally implanted in the chest wall region, where there is no bony continuity to offer counter-pressure. This makes effective compression more difficult to achieve.

Furthermore, scars in the chest heal sub-optimally in comparison to those on the limbs or face. Such scars for cardiac devices are below the collar bone (clavicle) or over the chest wall which is often visible. Hence the cosmetic appearance of the patient at such surgical sites is often of concern. In addition, most patients undergo reoperation for battery replacement every 6-8 years. Each surgery can result in a new scar.

SUMMARY

An aspect of an embodiment of the present disclosure provides, but is not limited to an inexpensive, reliable, and easy to operate a compression apparatus (and related system and method) for preventing or minimizing hematomas, keloids, scarring or proliferative scarring and swelling with concomitant suspension capabilities (e.g., a suspension system or suspension mechanism) at any post-operative stage. An aspect of an optional embodiment of the present disclosure includes an apparatus, system, and method having the ability to provide visual read outs of pressure applied to the site with a feedback sensor (if deployed) through a graphical user interface (GUI).

Hematomas, keloids and swelling (collectively herein, "hematomas") can be mitigated or treated by consistent and firm application of pressure to an intended site for a period of time as permitted by patient tolerance. Several aspects of this disclosure contemplate taking a surgical balloon in its uninflated state, placing it over a surgical site, securing the balloon in relation to a suspension system, and then inflating it with a fluid, which may be a gas or a liquid. At least two pressures are involved: a balloon pressure and a compression pressure that represents a force applied through the inflated balloon upon the surgical site. The compression force is a combination of two forces: 1. Lateral force exerted by straps under tension that engage the balloon—either through an elasticized skirt, slits in a skirt or one or more straps that overlie the balloon and 2. Direct downward force over the surgical site. Preferably, the balloon has an upper surface that is rigid and a basal surface that is flexible to allow for unidirectional balloon expansion.

To assure satisfactory strap tensioning, several alternative visual readouts or cues are contemplated to provide feedback indicating a satisfactory amount of strap tension to exert a satisfactory pressure on the apparatus. The first visual clue is embedded in slots provided in the balloon frame, where their distortion can provide feedback to the user for the lateral stretch on the balloon. The second visual clue may be embedded in the straps where the degree of stretch will modify the visual feedback. The third visual clue is in the balloon frame apparatus, which will indicate the degree of inflation or downward pressure on the surgical site. Such feedback cues can include distortion of a printed symbol or a color change with increasing pressure/stretch or another simplified visual cue. One or more of the clues can serve as feedback for proper placement and adjustment of the system. Alternatively, a strain gauge-based sensor may signify mechanical deformation of the balloon in response to a side stretch produced by the straps.

Another approach to providing visual cues of compressive forces includes use of an ink pellet filled with for example povidone iodine or any other medically safe colored liquid at the undersurface of the balloon. The pellet will burst at a certain minimum level of pressure. The ink would then get distributed along a contained space such as veins which run from the center of the underbelly of the balloon to the sides and stain them. Such an approach resembles a positive pregnancy test if a certain minimum amount of pressure is applied which leads to the ink pellet bursting into a confined space Clinical studies are underway to further optimize apparatus shape and ensure uniform pressure application with the aim of reducing the hematomas. An adjunctive benefit would be to study the cosmetic effect of scar healing with this apparatus and method. This is expected to derive from the uniform and reliable application of pressure, which is hypothesized to result in better scar approximation.

An aspect of an embodiment of the present disclosure provides, but is not limited to an inexpensive, reliable, and easy to operate a compression apparatus (and related system and method) for hematoma/swelling prevention with a suspension system or suspension mechanism independent of the characteristics of the underlying surface.

Yet another aspect of an embodiment of the present disclosure provides, but is not limited to a pressure apparatus (and related system and method) to reduce hematomas, keloids and swelling and improve cosmetic healing following implantation of cardiac electronic devices (CIEDs).

A further aspect of an embodiment of the present disclosure provides, but is not limited to, a compression apparatus (and related system and method) to reduce swelling and improve cosmetic healing following a surgical implant, or other related surgical procedures or medical conditions.

Although illustrative embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

BRIEF DESCRIPTION OF THE DRAWINGS

FIG. 10 details illustrative balloon specifications;

DETAILED DESCRIPTION

Figure 1A:
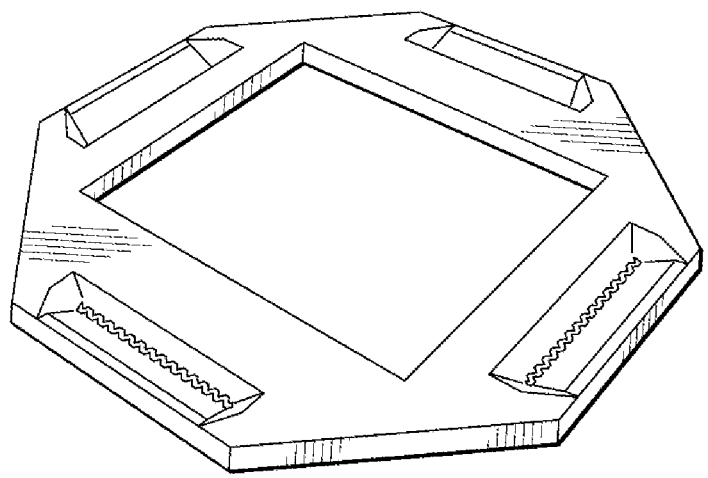
FIG. 1A is a 3-D semi flexible frame according to one alternative embodiment of the present disclosure (preferably, the frame is monolithic as in FIG. 1B, with a basal surface of the balloon)

As required, detailed embodiments of the present invention are disclosed herein; however, it is to be understood that the disclosed embodiments are merely exemplary of the invention that may be embodied in various and alternative forms. The Figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

While exemplary embodiments are described, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the apparatus and related components discussed herein may take on all shapes along the entire continual geometric spectrum of manipulation of x, y and z planes to provide and meet the environmental, anatomical, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned Figures, the apparatus may constitute various sizes, dimensions, contours, rigidity, shapes, flexibility and materials as it pertains to the components or portions of components of the apparatus, and therefore may be varied and utilized as desired or required.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, some terminology will be used for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in an apparatus or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5).

Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

Figure 1B:
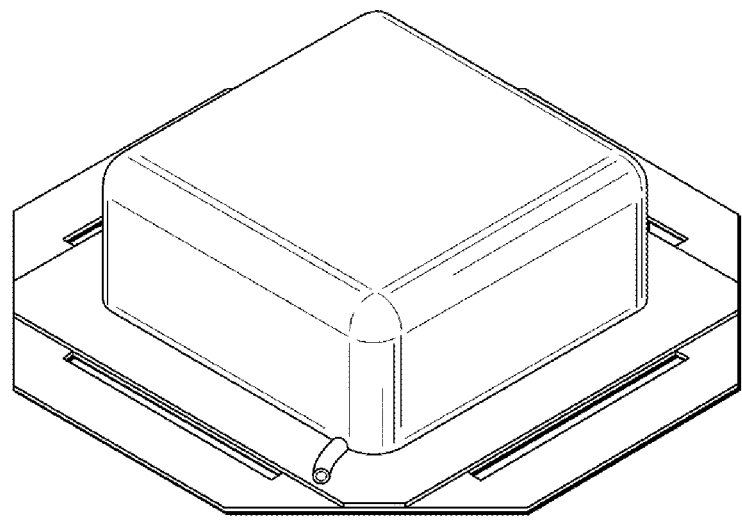
FIG. 1B depicts an illustrative medical balloon with a skirt in a pre-inflated state (in this embodiment, the balloon and the frame/skirt are one part)

In one embodiment, for example, the apparatus is applied to the intended site with a medical balloon facing outward. A semi-flexible frame for balloon securement was printed at UVA Biomedical Engineering Lab from NinjaFlex material (FIG. 1A). A medical silicone balloon was manufactured from biocompatible materials by Polyzen, Inc. Medical Device Developer and Manufacturer, Apex. NC based on design depicted in FIG. 1B. Although depicted as an octagon (eight-sided polygon), the frame/skirt may usefully have other polygonal perimeters or a curved perimeter that may assume a rounded, oval, elliptical or another curved perimeter. The silicone balloon is not applied to the skin directly, but through a suitable ointment or medical gauze covering the wound (as per post-procedure protocol) which is part of standard clinical care.

In an alternative embodiment, the frame is effectively a skirt that extends at least partially around and extends laterally away from a lower or basal face of a balloon. In this design, the balloon and the skirt are monolithic. The skirt when suitably expanded may have the optional ability for direct strapping over the landing pads.

In an embodiment, a modified sling is part of the apparatus to facilitate post surgical shoulder restriction as the clinical situation demands. The sling may be an arm cuff, forearm cuff, or wrist cuff which can be adhered to one of the adhesive landing pads, thus minimizing the material needed on the patient's arm and allowing for comfort with reliable shoulder restriction for the intended period or duration. In an embodiment, the sling may be attached or in communication with any stable body surface or inanimate surface. In an embodiment, for example, the sling may be attached or in communication with abdomen surface or upper back surface or the hospital bed or railing.

Figure 2:
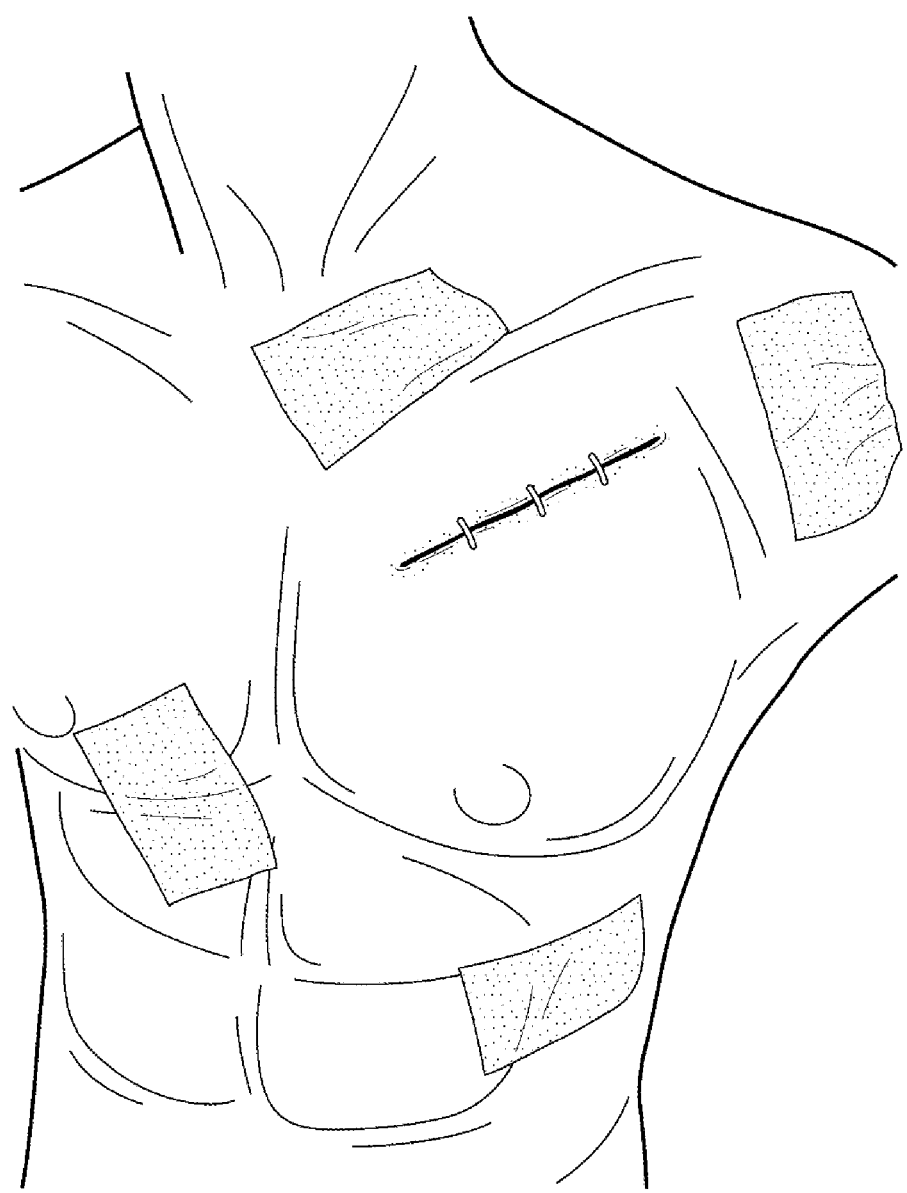
FIG. 2 is an environmental view that suggests a surgical scar and landing pads placed therearound for supporting tensioning straps.

One set of method steps (see FIG. 2) includes, not necessarily in this sequence:

Step 1: Placing four (or another specified number such as greater than or less than four as desired or required) adhesive pads or films around the incision site.

Figure 3:
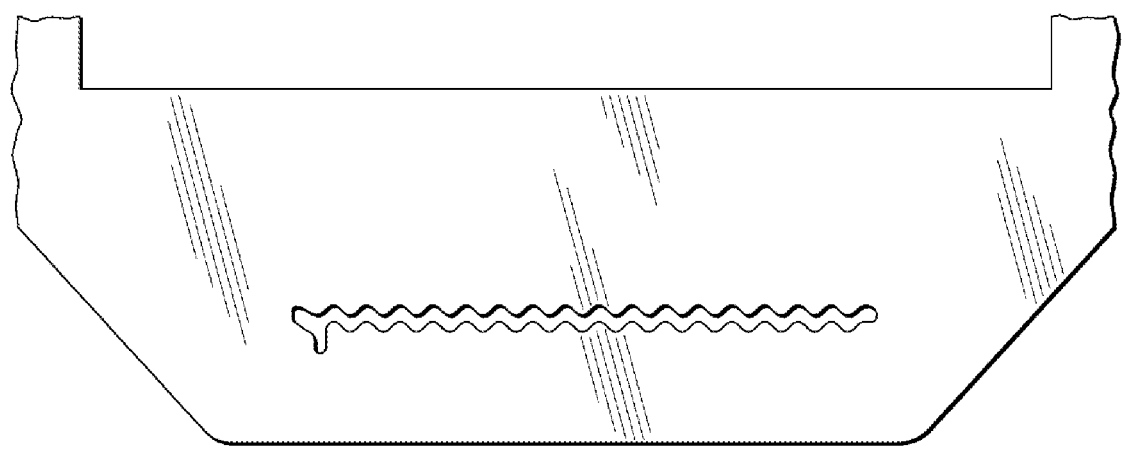
FIG. 3 shows a slit located in a portion of a balloon skirt through which a tensioning strap may be threaded.
Figure 4:
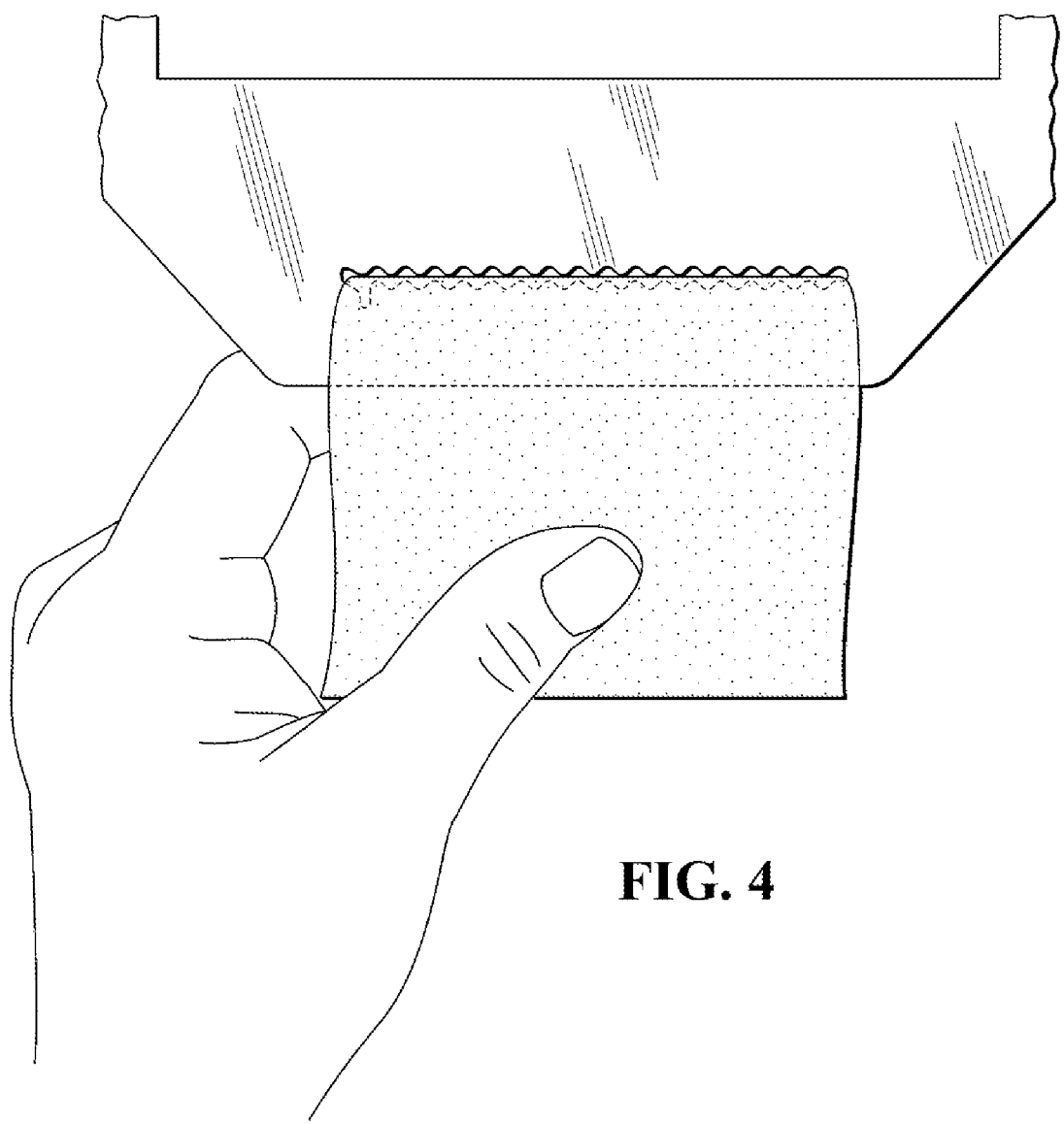
FIG. 4 illustrates part of a tensioning strap that is threaded through a slit.

Step 2: Looping four (or another specified number) straps (e.g., sleeve, belt, or loop) through slits that in one alternative embodiment may have teeth clasps located on the frame or balloon skirt (See FIGS. 3 and 4). It should be appreciated that less than or greater than four straps may be used as desired or required with the frame. Multiple frames may be deployed if desired. The straps are affixed on the landing pad either directly or via an inbuilt collapsible suspension/slot system which allows the straps to fold back upon themselves to varying degrees depending on the amount of required stretch, and provide a consistent surface area of intended contact to exert a reliable compressive force. The suspension system is collapsible and is preferably made of atraumatic medically inert material to avoid pressure points or reactions on the patient.

Figure 5:
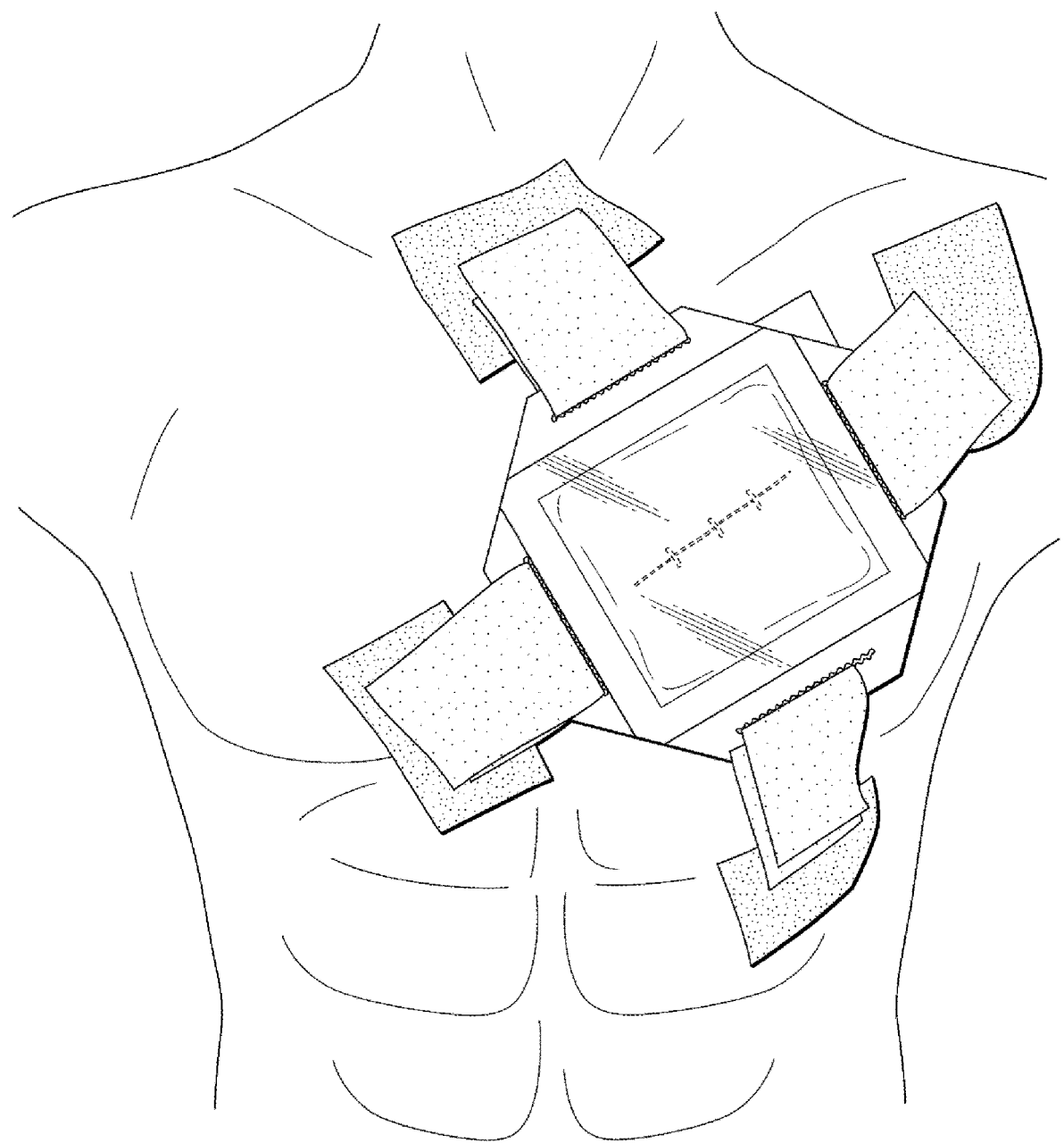
FIG. 5 is a perspective view of a transparent balloon with a skirt that engages tensioning straps that extend towards the landing pads according to one alternative embodiment.

Step 3: Placing the apparatus on the incision/surgical/intended target site with the balloon facing towards the site (See FIG. 5). Preferably, the balloon is transparent, clear, or translucent, such that it provides the advantage of viewing the hematoma, sensor, and/or body region. The balloon may be placed on the surgical site after a medically effective ointment or other lotion is applied to the surgical wound. Alternatively, a gauze-like material may cover the site before balloon emplacement.

Figure 6:
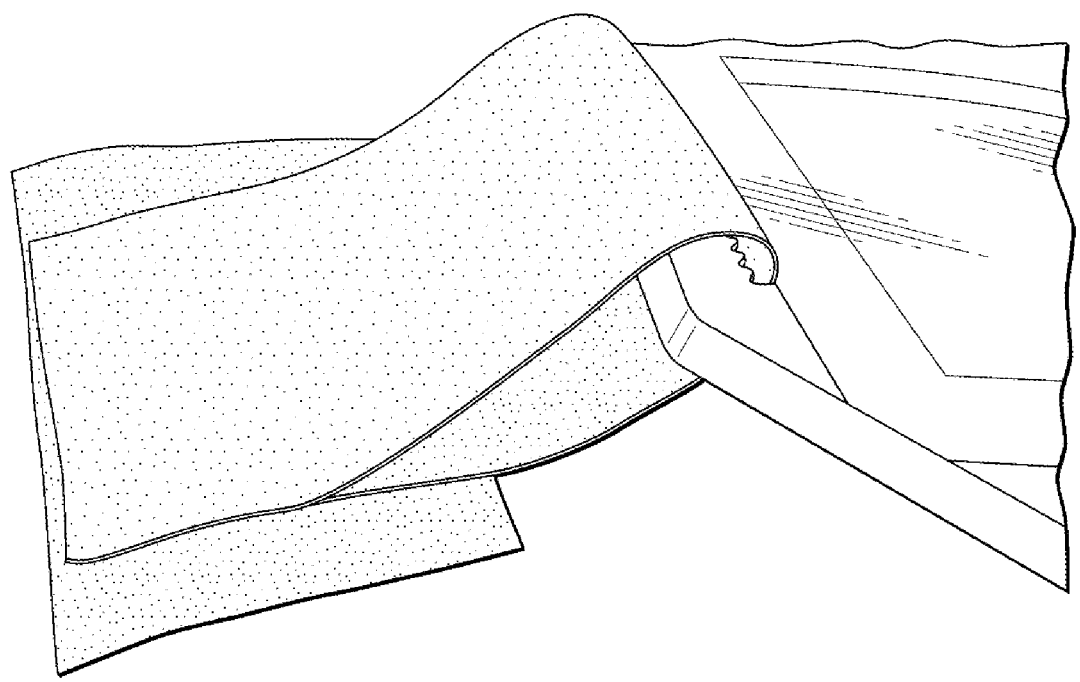
FIG. 6 illustrates one of the pads in its state of adhesion to end portions of a tensioning strap.
Figure 7:
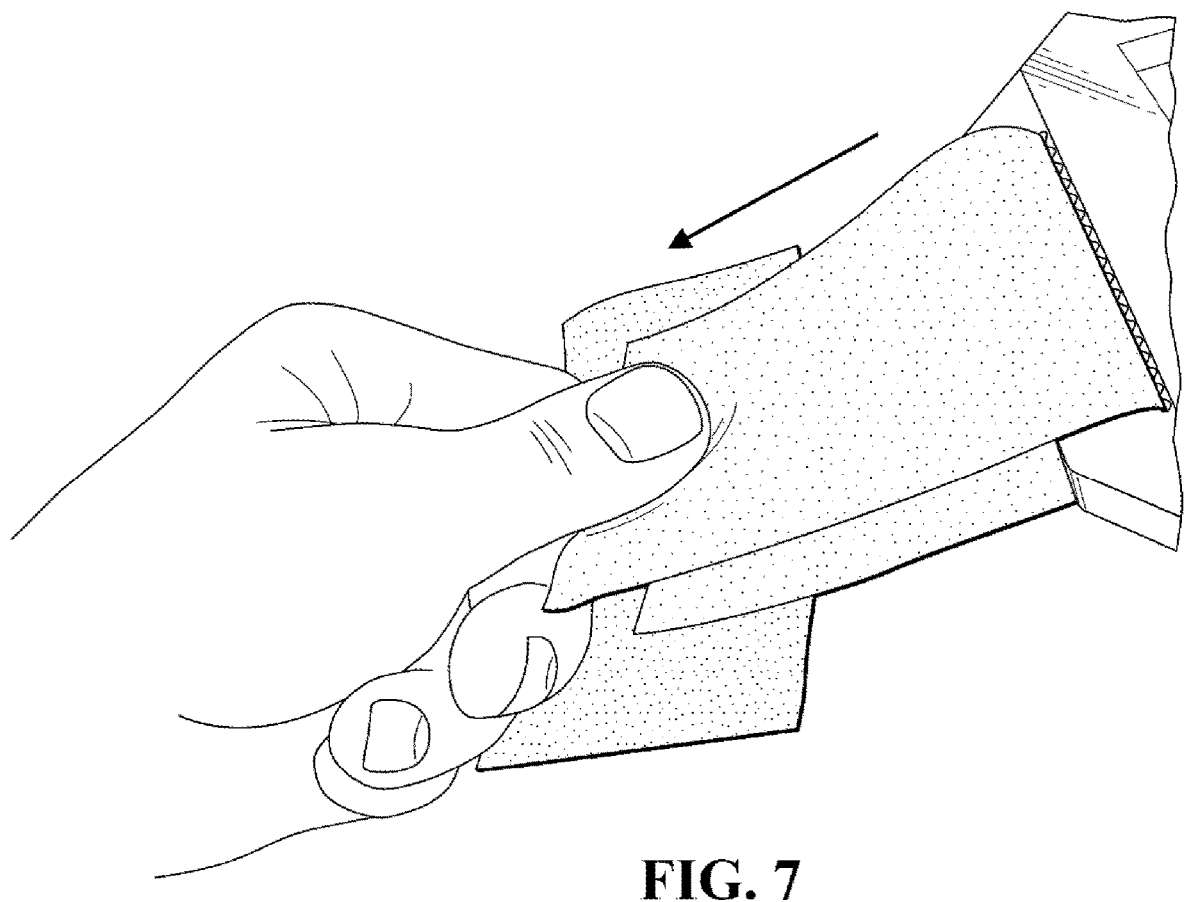
FIG. 7 suggests tensioning being applied to a length of a strap after one end thereof is secured to a pad, an intermediate strap section passes through a slit and an active end of the strap receives a tensioning force.

Step 4: Adjusting tension by pulling one end of the strap (e.g., sleeve, belt, or loop), thereby creating the suspension system or suspension mechanism (see FIGS. 6 and 7). If desired, a small bridge may be disposed on the landing pads which could serve as a fulcrum or pivot for the sleeves (e.g., sleeve, belt, or strap). There are several alternative ways to provide a visual indicator of a satisfactory stretch, i.e., a reliable pressure exerted by the apparatus on the surgical site. One visual clue may be embedded in the slots of the balloon frame where the distortion can provide feedback to the user. The second alternative visual clue may be embedded in the straps where the degree of stretch will modify the visual feedback. The third alternative visual clue is in the balloon frame apparatus which will indicate the degree of inflation or downward pressure on the surgical site. Such feedback cues can include a distortion of a printed symbol or a color change with increasing pressure/stretch or another simplified visual cue. One or more of the clues can be employed as feedback for proper placement and adjustment of the system. Early clinical testing has suggested that a baseline lateral stretch can increase the efficacy of downward pressure on the intended site with lower volumes of inflation.

Step 5: Optionally placing a pressure sensor under the apparatus to detect compressive forces and send a signal to a suitable receiver that indicates the sensed pressure. Illustrated is one type of suspension system or suspension mechanism that includes a sub-balloon pressure sensor in communication with an optional GUI and a balloon inflation pressure gauge with the same or another optional GUI. It will be appreciated that the sub-balloon pressure sensor need not be co-located with the pressure gauge. One such device is available under the name Kikuhime. As noted earlier, an embodiment, the balloon may be made of the same material as the frame or be monolithic therewith.

Figure 8:
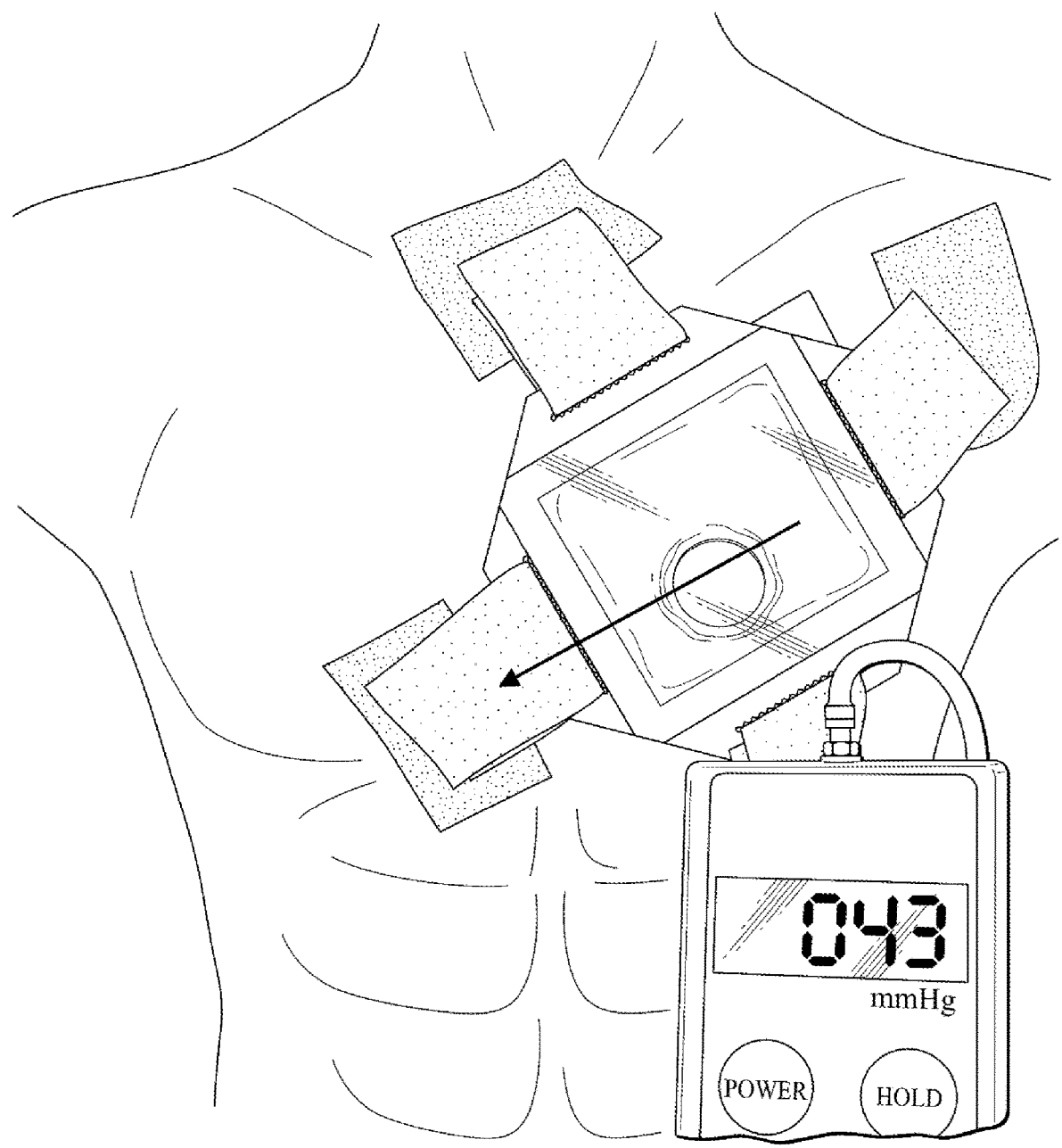
FIG. 8 illustrates optional placement of one from of a pressure feedback sensor that may underlie that balloon to sense pressure exerted upon the surgical scar (other means for offering visual cues as to strap tension are described but not depicted)

Referring to FIG. 8, for example, the (optional) sensor is illustrated as being external to the patient (subject). If desired, the sensor may be implanted in the patient (subject). Alternatively, a sensor may be implanted internally within the patient (subject) and another sensor may be implanted on the outside of the patient (subject). If desired, a plurality of sensors may be utilized. Optionally, multiple pressure meters (or processors or other hardware or software) may be utilized.

Figure 9:
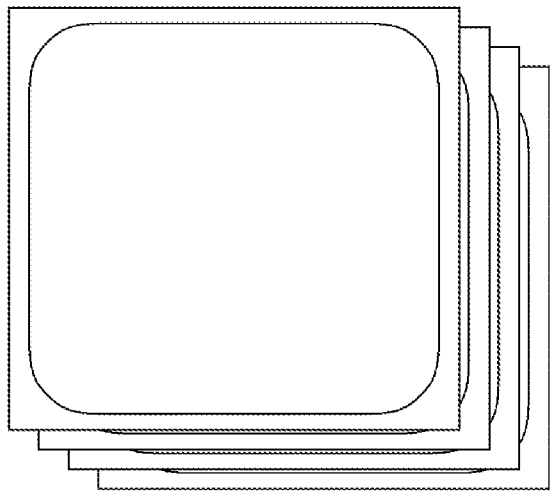
FIG. 9 depicts a conventional tissue retention package.
Figure 9:
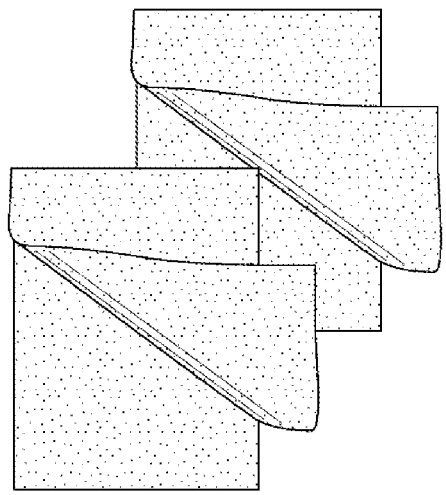

An aspect of an embodiment that may utilize related components is disclosed in U.S. Pub. No 20220104988, entitled "Tissue Retention System and Methods". This publication is incorporated by reference. An aspect of an embodiment that may utilize other components related to the TRS straps or pads may be obtained under the name of Stetrix Tissue Retention Package. See, e.g., stetrix.com. See FIG. 9.

An aspect of an embodiment of this disclosure may utilize components and aspects related to a Polyzen balloon, such as one that includes a polyether polyurethane film (Part #: SIP1-133). See, e.g., www.polyzen.com. Details of a suitable medical balloon appear in FIG. 10.

In one set of experiments, 160 patients were subjected to placement of a device for 4 hours and a pressure of 40 mmHg. (IRB #21759). Pressure was assessed every 30 minutes using a sphygmomanometer. The pressure sensor probe was placed under the subject apparatus. Pressure was added if the sensed pressure dropped. This pilot trial confirmed safety, tolerability, ease of application and removal. It showed lower swelling rates, which were systematically assessed by an instrument called a durometer and a signal for improved wound healing. The durometer enabled an assessment to be made of skin recoil and turgor, which is a metric for skin healing. Such indicia were improved in the balloon group. If desired, we add introducing an embedded durometer could be introduced into the balloon. It will be appreciated that the 4-hour period was selected arbitrarily. However, the durometer could provide feedback and thus enable the amount of time needed to be monitored. This would permit customizing the time and pressure required on an individual patient, thereby allowing for tailored therapies.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements.

Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein.

Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. A post-surgical wound treatment method comprising the steps of:
    positioning adhesive pads around a surgical site;
    locating a frame-supported balloon over the surgical site so that the frame surrounds the surgical site;
    adjusting orthogonally-oriented tensioning straps that lie between the adhesive pads and the frame to enable omnidirectional pressure to be exerted downwardly on the surgical site; and
    inflating the balloon to apply pressure to the surgical site.

2. The post-surgical wound treatment method of claim 1, further comprising the steps of:
    communicating a pressure sensor with one or more of the tensioning straps for detecting pressure exerting by the strap upon the balloon; and
    linking the pressure sensors with a graphical user interface so that the graphical user interface signifies via one or more visual cues the pressure exerted by the balloon upon the surgical site.

3. The post-surgical wound treatment method of claim 1, wherein the frame defines an aperture in a central region thereof.

4. The post-surgical wound treatment method of claim 1, wherein the balloon has a flexible contact surface to be positioned upon the surgical site.

5. The post-surgical wound treatment method of claim 1, wherein the frame includes strap-receiving slots.

6. The post-surgical wound treatment method of claim 5, wherein the orthogonally-oriented tensioning straps extend between the adhesive pads and the strap-receiving slots.

7. The post-surgical wound treatment method of claim 5, wherein the strap-receiving slots include two pairs of strap-receiving slots.

8. The post-surgical wound treatment method of claim 5, wherein the frame and the balloon are monolithic.

9. The post-surgical wound treatment method of claim 1, wherein the orthogonally-oriented tensioning straps include two pairs of orthogonally-oriented tensioning straps.

* * * * *